United States Patent [19]

Yu et al.

[11] 4,105,783

[45] * Aug. 8, 1978

[54] THERAPEUTIC TREATMENT OF DRY SKIN

[76] Inventors: Ruey J. Yu, 4400 Dexter St., Philadelphia, Pa. 19128; Eugene J. Van Scott, 1138 Sewell La., Rydal, Pa. 19046

[*] Notice: The portion of the term of this patent subsequent to May 3, 1994, has been disclaimed.

[21] Appl. No.: 720,835

[22] Filed: Sep. 7, 1976

Related U.S. Application Data

[63] Continuation-in-part of Ser. No. 598,224, Jul. 23, 1975, Pat. No. 4,021,572.

[51] Int. Cl.$^2$ .............................................. A61K 31/35
[52] U.S. Cl. ..................... 424/283; 424/279; 424/285; 424/311; 424/316; 424/317; 424/320; 424/329
[58] Field of Search ............... 424/180, 283, 285, 316, 424/311, 317, 320

[56] References Cited

U.S. PATENT DOCUMENTS

| | | | |
|---|---|---|---|
| 2,118,566 | 5/1938 | De Wayne Miles | 424/317 |
| 2,717,850 | 9/1955 | Schmitz | 424/319 |
| 3,068,145 | 12/1962 | Glenn | 424/320 |
| 3,096,244 | 7/1963 | Ehrhart et al. | 424/320 |
| 3,124,506 | 3/1964 | Holman | 424/317 |
| 3,549,544 | 12/1970 | Johnson | 252/545 |
| 3,639,623 | 2/1972 | Ritschel et al. | 424/329 |
| 3,640,883 | 2/1972 | Gotte et al. | 424/320 |
| 3,666,863 | 5/1972 | Swanbeck | 424/317 |
| 3,806,593 | 4/1974 | Swanbeck et al. | 424/311 |
| 3,879,537 | 4/1975 | Van Scott et al. | 424/311 |

Primary Examiner—Leonard Schenkman
Attorney, Agent, or Firm—LeBlanc and Shur

[57] ABSTRACT

Preventive as well as therapeutic treatment to alleviate the symptoms of disorders characterized by cracking, flaking or scaling of the skin consisting of the topical application of a lotion, cream or ointment containing one or more of the $\alpha$- or $\beta$-hydroxy acids or $\alpha$-keto acids and esters thereof, their amides and their ammonium salts is disclosed. The compounds include free acid, amide and/or ammonium salt forms of citric acid, glycolic acid, glucoronic acid, galacturonic acid, glucuronolactone, gluconolactone, $\alpha$-hydroxybutyric acid, $\alpha$-hydroxyisobutyric acid, lactic acid, malic acid, mandelic acid, mucic acid, pyruvic acid, methyl pyruvate, ethyl pyruvate, $\beta$-phenyllactic acid, $\beta$-phenylpyruvic acid, saccharic acid, tartaric acid, tartronic acid, and $\beta$-hydroxybutyric acid. The therapeutic compOsition may include one or more of the compounds present in the total amount of from one to twenty percent. Topical application to affected areas has been found to achieve amelioration of the dry skin.

15 Claims, No Drawings

THERAPEUTIC TREATMENT OF DRY SKIN

This application is a continuation-in-part of our copending patent application Ser. No. 598,224, filed July 23, 1975 now U.S. Pat. No. 4,021,572, hereby incorporated by reference, and is related to our copending applications Ser. Nos. 556,423 and 556,424, filed Mar. 7, 1975, now U.S. Pat. Nos. 3,988,470 and 3,984,566, respectively, which are divisions of application Ser. No. 445,231, filed Feb. 25, 1974, now U.S. Pat. No. 3,920,835, which in turn was a continuation-in-part of application Ser. No. 394,269, filed Sept. 4, 1973, now U.S. Pat. No. 3,879,537.

This invention relates to a treatment for skin disorders characterized by cracking, flaking or scaling of hands, feet or the body commonly known as "dry skin", and specifically to compounds which have been found to be effective when topically applied to prevent as well as heal the skin lesions associated with these conditions in humans.

Severe "dry skin" conditions known as ichthyosis are hereditary disorders. The term ichthyosis alludes to a fish scale-like appearance of the human skin. Ichthyosis, characterized by a "dry skin" appearance, is usually detected during the early years of childhood. Small, fine scales with a "pasted-on" appearance are found most prominently on the trunk and upper extremities. Larger, more adherent scales are present on the legs. Only a small number of the population are affected by this hereditary disorder.

In contrast to ichthyosis, mild to moderate "dry skin" conditions are quite common among the population. These common "dry skin" conditions are specially pronounced during the fall and winter seasons, when environmental humidity is comparatively low. They are characterized by fissures, chaps, cracks or flakes of the skin on hands, face, neck and legs.

Conventional treatments for all kinds of dry skin conditions primarily involve the topical application of oils or oil preparations, and hydrating emollients. In addition, ointments containing salicylic acid, urea, glycerol, propylene glycol, sorbitol or vitamin A have been used. Prior treatments, however, have not been universally successful, and have, in many cases, been unable to promote healing to cause a complete remission of the symptoms. Because the mechanisms involved in causing dry skin are not known, treatment has usually resulted in a temporary remission or healing of the flaky or scaly lesions.

We have now discovered that "dry skin" conditions may be successfully prevented or treated with the acid, amide or ammonium salt of $\alpha$- or $\beta$-hydroxyacids or $\alpha$-keto acids and esters thereof. The compounds of the present invention include citric acid, glycolic acid, glucuronic acid, galacturonic acid, glucuronolactone, gluconolactone, $\alpha$-hydroxybutyric acid, $\alpha$-hydroxyisobutyric acid, lactic acid, malic acid, mandelic acid, mucic acid, pyruvic acid, methylpyruvate, ethyl pyruvate, $\alpha$-phenylactic acid, $\alpha$-phenylpyruvic acid, saccharic acid, tartaric acid, tartronic acid, and $\alpha$-hydroxybutyric acid. Generally, the amide may be formed from acid anhydride or lactone and ammonia or any organic primary or secondary amine. The ammonium salt may be formed directly from acid and an organic primary, secondary or tertiary amine.

Preferred organic primary amines include any alkylamines such as methylamine and ethylamine; ethanolamines such as monoethanolamine and monoisopropanolamine; and diamines such as ethylenediamine and 1,2-diaminopropane.

Preferred organic secondary amines include dialkylamines such as dimethylamine and diethylamine; diethanolamine and diisopropanolamine; N-methylethanolamine and N-ethylethanolamine.

Preferred organic tertiary amines include trialkylamines such as trimethylamine and triethylamine; triethanolamine; N-methyldiethanolamine and triisopropanolamine.

It has been established through tests on humans having "dry skin" conditions that topical application of a lotion, cream or ointment containing from 1 to 20 percent of at least one acid, the ester or the amide or the ammonium salt of the present invention and preferably from 2 to 10 percent thereof, is therapeutically effective, when applied on a daily basis, to cause, within about one to two weeks, a return of the affected areas to a normal skin condition. If two or more acids, amides or ammonium salts are used in a composition of the invention, the total concentration of the compounds is preferred not to exceed 10 percent by weight of the composition. It has also been found in humans having frequent occurrence of cracking or flaking skin that topical application of the aforementioned composition of the present invention is effective, when applied on a daily basis, in preventing development of dry skin lesions.

Accordingly, it is the object of this invention to provide a cosmetic composition containing at least one of the acids, the amides and/or the ammonium salts, which when topically applied will reliably prevent the development of dry skin conditions.

It is another object of this invention to provide a medicinal composition containing at least one of the acids, the amides and/or the ammonium salts which when topically applied will substantially alleviate the symptoms of dry skin.

It is still another object to provide a method for treating dry skin with a nonirritant and nontoxic lotion, cream or ointment of the present invention.

It is still another object to provide a safe and efficient method for treating the symptoms of dry skin through regular topical application of a medicinal composition which will promote healing within about one to two weeks.

It is still another object of this invention to provide a method for formulating a cosmetic as well as medicinal composition in lotion, cream or ointment which when topically applied at least daily to skin areas prone to lesions of cracking, flaking or scaling will prevent the development of dry skin or result in a restoration of normal healthy skin condition.

PREPARATION OF THE THERAPEUTIC COMPOSITIONS

Previously, in treatment of extremely dry skin conditions such as ichthyosis, $\alpha$- or $\beta$-hydroxyacids or $\alpha$-ketoacids were prepared in a composition containing 5 to 10 percent by weight of the compounds in a cream or ointment. The pH of the composition was about 2 or less. In treatment of common dry skin conditions according to this invention we found that the above composition with low pH could cause some skin irritation (redness and sensation of burning) on some of the sensitive subjects. It was therefore desirable to develop compositions which were therapeutically effective but not irritative.

Most inorganic alkalis, forming inorganic salts with α- or β-hydroxyacids or α-ketoacids that do not readily penetrate human skin, cannot be used to neutralize these acids. It has previously been discovered that certain organic bases, and ammonium hydroxide, may be successfully used to raise the pH of the compositions containing α- or β-hydroxy acids or α-ketoacids without compromising the therapeutic efficaciousness of the active ingredients. Under such conditions the active ingredients are in the form of amide or ammonium salt. The organic bases may include any organic amine of primary, secondary or tertiary family. The organic primary amines may include any alkylamines such as methylamine and ethylamine; and ethanolamines such as monoethanolamine and monoisopropanolamine; any diamines such as ethylenediamine and 1,2-diaminopropane. The organic secondary amines may include dialkylamines such as dimethylamine and diethylamine; diethanolamine and diisopropanolamine; N-methylethanolamine and N-ethylethanolamine. The organic tertiary amines may include trialkylamines such as trimethylamine and triethylamine; triethanolamine; N-methyldiethanolamine and triisopropanolamine.

The α and β-hydroxyacids, α-ketoacids and the esters of the present invention include citric acid, glycolic acid, glucuronic acid, galacturonic acid, glucuronolactone, gluconolactone, α-hydroxybutyric acid, α-hydroxyisobutyric acid, lactic acid, malic acid, mandelic acid, mucic acid, pyruvic acid, methyl pyruvate, ethyl pyruvate, β-phenyllactic acid, β-phenylpyruvic acid, saccharic acid, tartaric acid, tartronic acid and β-hydroxybutyric acid.

Generally, a nonirritating composition of this invention should have a pH of the lotion, cream or ointment between 3.5 and 7.5.

To prepare an amide or an ammonium salt of the present invention the lactone or the hydroxyacid or the ketoacid is allowed to react at room temperature with ammonium hydroxide or an organic amine in aqueous or alcoholic aqueous solution. Generally, the amide or ammonium salt thus formed needs no isolation procedure and may be directly incorporated into the therapeutic composition.

The initial concentration of α or β-hydroxyacid or α-ketoacid may range from 1 to 20 percent by weight of the total composition. The preferred concentration range, however, is from 2 to 10 percent.

Ordinary distilled water may be used as a solvent in the preparation of the composition. The concentration of the solvent may range from 5 to 30 percent by volume of the total composition.

In a variety of methods for formulating a composition of the present invention two or more than two different amides or ammonium salts may be utilized in the composition.

The prophylactic as well as therapeutic composition may be prepared in a form of lotion, cream or ointment. In these instances, cosmetically acceptable ingredients are incorporated into the formulation, and lotions, creams or ointments are readily prepared.

The following are illustrative examples of formulations of compositions according to this invention. Although the examples utilize only selected formulations useful according to this invention, it should be understood that the following examples are illustrative and not limited. Therefore, any of the aforementioned acids, esters and amines may be substituted according to the teachings of this invention in the following formulations.

EXAMPLE 1

Glycolic acid, 5 grams was dissolved in 10 ml water and ethanolamine, 3 ml was added to partially neutralize the acidity of the solution. This solution was admixed with 82 grams of water-nonwashable lotion prepared from mineral oil, cottonseed oil, isopropyl palmitate and water with a surfactant such as sorbitan sesquioleate. The ingredients of said lotion are present in 15:15:5:60:5 parts by weight, respectively. The lotion thus prepared is stored in a plastic squeeze bottle having a nozzle attached thereto.

EXAMPLE 2

Lactic acid, USP grade 5 ml was dissolved in 10 ml of water and triethanolamine, 5 ml was added to neutralize partially the acidity of the solution. This solution was admixed with 80 grams of water-nonwashable lotion prepared from mineral oil, cottonseed oil and water with a surfactant such as sorbitan sesquioleate. The ingredients of said lotion are present in 30:15:50:5 parts by weight respectively.

EXAMPLE 3

Part A:
  Polyoxyethylene (20) sorbitan monooleate (hereinafter Tween 80): 5 gm
  Cetyl alcohol: 20 gm
Part B:
  Water: 45 ml
  Propylene glycol: 10 ml
  Glycolic acid: 10 gm
  Ethanolamine: 7 ml
Heat Part A to 75° C and heat Part B to 75° C. Add Part B slowly to Part A with agitation. Continue agitation until the mixture is congealed. The water-washable cream thus prepared has a pH of 4.7.

EXAMPLE 4

Part A:
  Tween 80: 5 gm
  Cetyl alcohol: 22 gm
Part B:
  Water: 55 ml
  Propylene glycol: 10 ml
  Lactic acid: 5 ml
  Ethanolamine: 2 ml
Heat Part A to 75° C and heat Part B to 75° C. Add Part B slowly to Part A with agitation. Continue agitation until the mixture is congealed. The water-washable cream thus prepared has a pH of 4.5.

EXAMPLE 5

Part A:
  Tween 80: 5 gm
  Cetyl alcohol: 15 gm
  Stearyl alcohol: 5 gm
Part B:
  Water: 60 ml
  Propylene glycol: 5 ml
  Citric acid: 2 gm
  Lactic acid: 2 ml
  Glycolic acid: 2 gm
  Ethanolamine: 3 ml
Heat both Part A and Part B to 75° C. Add Part B slowly to Part A with agitation. Continue agitation until the mixture is congealed. The water-washable cream containing three active ingredients has a pH of 4.4.

EXAMPLE 6

Glycolic acid, 7 grams was dissolved in 10 ml of ice water and ethanolamine, 5 ml was added to neutralize partially the acidity of the solution. This solution was admixed with 78 grams of water-nonwashable ointment prepared from petrolatum, mineral oil, spermaceti and water with a surfactant such as sorbitan sesquioleate. The ingredients of said ointment are present in 10:10:6:68:6 parts by weight, respectively.

EXAMPLE 7

Lactic acid, USP grade 5 ml was dissolved in 10 ml of ice water and triethanolamine, 4 ml was added to neutralize partially the acidity of the solution. This solution was admixed with 81 grams of water-nonwashable ointment prepared from petrolatum, mineral oil, isopropyl myristate, spermaceti and water with a surfactant such as sorbitan sesquioleate. The ingredients of said ointment are present in 10:10:10:6:58:6 parts by weight, respectively.

EXAMPLE 8

$\alpha$-Hydroxyisobutyric acid, 5 grams and sorbitol 2 grams were dissolved in 8 ml of water. This solution was admixed with 85 grams of water-nonwashable ointment prepared from petrolatum, mineral oil, spermaceti and water with a surfactant such as sorbitan sesquioleate. The ingredients of said ointment are present in 10:10:6:68:6 parts by weight, respectively.

EXAMPLE 9

Pyruvic acid 2 ml, glycolic acid 2 grams, citric acid 2 grams, and lactic acid 2 ml were dissolved in 12 ml of water. This solution was admixed with commercially available USP grade hydrophilic ointment (80 grams) to a uniform consistency. A water-washable ointment thus prepared contained four active ingredients.

TEST RESULTS

(A) Severe Dry Skin

Ten patients with severe dry skin conditions such as ichthyosis were instructed first to wet the body by taking a shower and then apply a thin film of the compositions formulated according to Examples 4, 7 or 9 on left side of the body. Other commercially available preparations such as vegetable oil or petrolatum were applied on right side of the body. Twice daily topical application was continued for several weeks. In all the patients tested the left side of the body became less flaky and felt smoother than the right side after about a week of topical treatment. The rough and flaky lesions on the left side of the body were substantially clear after ten days of treatment. The left side of the body devoid of any cracking, flaking or scaling usually reached an improved state comparable to normal appearing skin within two to three weeks after initial treatment. Very little or no substantial improvement was seen on the right side of the body, which had been treated with vegetable oil or petrolatum alone. Therefore after three weeks the patients were instructed to apply the composition of the present invention on the right side of the body. Again, the skin on the right side of the body became normal appearing within two to three weeks.

Once a normal appearing skin was restored, it remained improved for from several weeks to several months, varying from patient to patient, without further application of the ointment. It was, however, necessary to continue the application of the ointment in order to maintain the skin free from recurrence of the overt disease.

(B) Common Dry Skin

Human subjects with mild to moderate degrees of dry skin conditions, as evidenced by dry, cracking or flaking of the skin, were instructed to apply topically the lotion, cream or ointment of the present invention formulated according to Examples 1 through 8 on the affected skin areas. Twice daily topical application was continued for a few weeks. In all the twenty-three human subjects tested the feeling of the skin dryness disappeared after three to four days of topical treatment. In twenty-one human subjects tested the rough and cracked skin usually became less pronounced within a week time. Generally the skin appeared normal and felt smooth after about two weeks of topical treatment.

In contrast to the severe dry skin disease the common dry skin conditions once restored to normal appearing skin remained improved for some time until causes of dry skin, such as low humidity, cold weather, detergents, soaps, chemicals, etc., recurred. On continued use it was also found that twice daily topical application of a composition of the present invention prevented the development of new dry skin lesions.

The invention may be embodied in other specific forms without departing from the spirit or essential characteristics thereof. The present embodiment is, therefore, to be considered in all respects as illustrative and not restrictive, the scope of the invention being indicated by the appended claims rather than by the foregoing description, and all changes which come within the meaning and range of equivalency of the claims are, therefore, intended to be embraced therein.

What is claimed and desired to be secured by United States Letters Patent is:

1. A non-irritating method for alleviating the symptoms of dry skin in humans comprising: topically applying to involved areas of the body an effective amount of a composition comprising: a therapeutically effective amount of a product prepared by reacting, in aqueous or alcoholic aqueous solution at least one member selected from the group consisting of citric acid, glycolic acid, glucuronic acid, galacturonic acid, glucuronolactone, gluconolactone, $\alpha$-hydroxybutyric acid, $\alpha$-hydroxyisobutyric acid, lactic acid, malic acid, mandelic acid, mucic acid, pyruvic acid, methyl pyruvate, ethyl pyruvate, $\beta$-phenyllactic acid, $\beta$-phenylpyruvic acid, saccharic acid, tartaric acid, tartronic acid, and $\beta$-hydroxybutyric acid and a base selected from the group consisting of ammonium hydroxide, an organic primary, secondary, or tertiary alkylamine, alkanolamine, diamine, dialkylamine, dialkanolamine, alkylalkanolamine, trialkylamine, trialkanol amine, dialkyl alkanol amine, or alkyl dialkanolamine wherein the alkyl or alkanol substituent has from 1 to 8 carbon atoms in a pharmaceutically acceptable vehicle.

2. The method of claim 1 wherein the reaction product is present in a concentration of from 1 up to about 20 percent by volume of the total composition.

3. The method of claim 1 wherein the reaction product is present in a concentration of from 2 up to about 10 percent by volume of the total composition.

4. The method of claim 1 wherein the reaction product comprises a reaction product of a member selected from the group consisting of citric acid, glycolic acid, glucuronic acid, galacturonic acid, glucuronolactone, gluconolactone, α-hydroxybutyric acid, α-hydroxyisobutyric acid, lactic acid, malic acid, mandelic acid, mucic acid, pyruvic acid, methyl pyruvate, ethyl pyruvate, β-phenyllactic acid, β-phenylpyruvic acid, saccharic acid, tartaric acid, tartronic acid, and β-hydroxybutyric acid and a member selected from the group consisting of ammonium hydroxide, methylamine, ethylamine, monoethanolamine, monoisopropanolamine, ethylenediamine, 1,2-diaminopropane, dimethylamine, diethylamine, diethanolamine, diisopropanolamine, N-methylethanolamine, N-ethylethanolamine, triethylamine, triethanolamine, N-methyldiethanolamine, and triisopropylamine.

5. The method of claim 1 wherein the vehicle is at least one member selected from the group consisting of water, ethanol, and propylene glycol present therein in a concentration of up to 99, 70, and 30 percent, respectively.

6. The method of claim 1 wherein the pH thereof is from 3.5 to about 7.5.

7. The non-irritating method of claim 1 wherein said composition comprises a reaction product of from about 5 to about 7 parts glycolic acid, and about 3 to about 5 parts ethanolamine in about 10 parts water per 100 parts of said vehicle.

8. The non-irritating method of claim 1 wherein said composition comprises a reaction product of about 5 parts lactic acid and about 4 to about 5 parts triethanolamine in about 10 parts water per 100 parts of said vehicle.

9. The non-irritating method of claim 1 wherein said composition comprises: a reaction product of about 5 parts glycolic acid and 3 parts ethanolamine in a vehicle of mineral oil, cottonseed oil, isopropyl palmitate, water, and a surfactant present in a ratio of 15:15:5:60:5 per 100 parts of said vehicle.

10. The non-irritating method of claim 1 wherein said composition comprises: a reaction product of about 5 parts lactic acid and 5 parts triethanolamine in 10 parts water in a vehicle of mineral oil, cottonseed oil, water, and a surfactant present in a ratio of 30:15:50:5 per 100 parts of said vehicle.

11. The non-irritating method of claim 1 wherein said composition comprises: a reaction product of 10 parts glycolic acid and 7 parts ethanolamine in 20 parts cetyl alcohol, 5 parts polyoxyethylene (20) sorbitan monooleate, 45 parts water, and 10 parts propylene glycol.

12. The non-irritating method of claim 1 wherein said composition comprises: a reaction product of 5 parts lactic acid and 2 parts ethanolamine in 22 parts cetyl alcohol, 5 parts polyoxyethylene (20) sorbitan monooleate, 55 parts water, and 10 parts propylene glycol.

13. The non-irritating method of claim 1 wherein said composition comprises: a reaction product of 2 parts citric acid, 2 parts lactic acid, 2 parts glycolic acid and 3 parts ethanolamine in 15 parts cetyl alcohol, 5 parts stearyl alcohol, 5 parts polyoxyethylene (20) sorbitan monooleate, 60 parts water, and 5 parts propylene glycol.

14. The non-irritating method of claim 1 wherein said composition comprises: a reaction product of 7 parts glycolic acid and 5 parts ethanolamine in 10 parts water in a vehicle of petrolatum, mineral oil, spermaceti, water, and a surfactant present in a ratio of 10:10:6:68:6 parts per 100 parts of said vehicle.

15. The non-irritating method of claim 1 wherein said composition comprises: a reaction product of 5 parts lactic acid and 4 parts triethanolamine in 10 parts water in a vehicle of petrolatum, mineral oil, isopropyl myristate, spermaceti, water, and a surfactant present in a ratio of 10:10:10:6:58:6 parts per 100 parts of said vehicle.

* * * * *

UNITED STATES PATENT AND TRADEMARK OFFICE

CERTIFICATE EXTENDING PATENT TERM
UNDER 35 U.S.C. 156

Patent No.     : 4,105,783

Dated          : August 8, 1978

Inventor(s)    : Ruey J. Yu et al

Patent Owner   : Westwood Pharmaceuticals Inc.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

541 DAYS with all rights pertaining thereto as provided by 35 USC 156 (b).

I have caused the seal of the Patent and Trademark Office to be affixed this 7th day of December 1990.

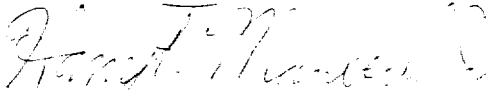

Harry F. Manbeck, Jr.
Assistant Secretary and Commissioner
  of Patents and Trademarks